United States Patent
Atwal et al.

[11] Patent Number: 5,547,966
[45] Date of Patent: Aug. 20, 1996

[54] ARYL UREA AND RELATED COMPOUNDS

[75] Inventors: Karnail S. Atwal, Newtown, Pa.; Francis N. Ferrara, Martinsville; Charles Z. Ding, Plainsboro, both of N.J.

[73] Assignee: Bristol-Myers Squibb Company, Princeton, N.J.

[21] Appl. No.: 134,195

[22] Filed: Oct. 7, 1993

[51] Int. Cl.$^6$ .................... A61K 31/44; C07D 213/02
[52] U.S. Cl. .................... 514/352; 514/353; 546/304; 546/306; 546/309
[58] Field of Search .................... 514/352, 353; 546/304, 306, 309

[56] References Cited

U.S. PATENT DOCUMENTS

| | | | |
|---|---|---|---|
| 4,057,636 | 11/1977 | Petersen | 546/306 |
| 4,405,644 | 9/1983 | Kabbe et al. | 424/322 |
| 4,491,595 | 1/1985 | Niemers et al. | 424/326 |
| 4,629,731 | 12/1986 | Lobbestael et al. | 546/306 |
| 4,988,723 | 1/1991 | Shiokawa et al. | 514/227.5 |
| 5,006,523 | 4/1991 | Atwal | 514/227.5 |
| 5,011,837 | 4/1991 | Atwal et al. | 514/227.8 |
| 5,061,813 | 10/1991 | Atwal | 549/399 |
| 5,140,031 | 8/1992 | Atwal et al. | 514/302 |
| 5,338,849 | 4/1994 | Festal et al. | 546/113 |

FOREIGN PATENT DOCUMENTS

| | | |
|---|---|---|
| 0005318 | 11/1979 | European Pat. Off. . |
| 0148536 | 7/1985 | European Pat. Off. . |
| 0205292 | 11/1985 | European Pat. Off. . |
| 0214818 | 3/1987 | European Pat. Off. . |
| 0274821 | 10/1988 | European Pat. Off. . |
| 0344747 | 12/1989 | European Pat. Off. . |
| 0350805 | 1/1990 | European Pat. Off. . |
| 0359537 | 3/1990 | European Pat. Off. . |
| 0370740 | 5/1990 | European Pat. Off. . |
| 0389861 | 10/1990 | European Pat. Off. . |
| 0405233 | 1/1991 | European Pat. Off. . |
| 0412531 | 2/1991 | European Pat. Off. . |
| 0477778 | 4/1992 | European Pat. Off. . |
| 0562796 | 9/1993 | European Pat. Off. . |
| WO87/07607 | 12/1987 | WIPO . |

OTHER PUBLICATIONS

H. J. Petersen et al., "Synthesis and Hypotensive Activity of N–Alkyl–N''–cyano–N'–pyridylguanidines", *J. of Med. Chem.*, vol. 21, No. 8, (Aug. 1978), pp. 773–781.

V. A. Ashwood et al., "Synethsis and Antihypertensive Activity of 4–(Cyclic amido)–2H–1–benzopyrans", *J. Med. Chem.*, (1986) 29, pp. 2194–2201.

C. R. Rasmussen et al., "Improved Procedures for the Preparation of Cycloalkyl–, Arylalkyl–, and Arylthioureas", *Synthesis*, (Jun. 1988), pp. 456–459.

V. V. Mozolis et al., "Preparation of N–Substituted Thiourea", *Russian Chem. Reviews*, 42 (7), (1973), pp. 587–595.

J. M. Evans et al., "Synthesis and Antihypertensive Activity of Substituted trans–4–Amino–3,4–dihydor–2, 2–dimethyl–2H–1–benzopyran–3–ols", *J. Med. Chem..*, (1983), 26, pp. 1582–1589.

R. W. Lang et al., "Synthesis of Selectively Trifluoromethylated Pyridine Derivatives as Potential Antihypertensives", *Helvetica Chimica Acta*, (1988), vol. 71, pp. 596–601.

P. Sebok et al., "Selective synthesis of Analogues of the Natural Precocenes, Synthesis and Regioselective (–Alkylation of 6–Chloro– and 6–Tert–Butyl–7,8–Dihyedroxy–2, 2–Dimethyl–4–Chromanones", *Heterocycles*, (1988), 27, pp. 2595–2607.

P. Teixidor et al., "Improved Preparation of Precocene II, Unexpected Results in the Reduction of Alkoxy Substituted Acetophenones and 4–Chromanones with Sodium Borohydride", *Heterocycles*, (1988), 27, pp. 2459–2465.

A. Banerji et al., "Enolates of o–Hydroxyacetophenones: Novel Synthesis of 2,2–Dialkyl–4–Chromanones", *Tetrahedron Letters*, No. 38, 1979, pp. 3685–3686.

G. Ariamala et al., "A Simple Route for the Synthesis of 4–Chlorochromenes and Chroman–4–ones", *Tetrahedron Letters*, (1988), vol. 29, No. 28, pp. 3487–3488.

W. H. Wagner et al., *Chemical Abstracts*, vol. 71, No. 17, 1969, #79470.

*Primary Examiner*—Yogendra N. Gupta
*Attorney, Agent, or Firm*—Ellen K. Park

[57] ABSTRACT

Compounds having the formula

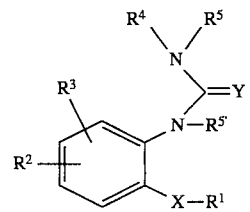

and pharmaceutically acceptable salts thereof wherein X is a single bond, O, CO, S, NH or N(lower alkyl); Y is O, S or NCN; and $R^1$ to $R^{5'}$ are as defined herein. These compounds have potassium channel activating activity and are useful, therefore for example, as cardiovascular agents.

5 Claims, No Drawings

ARYL UREA AND RELATED COMPOUNDS

BRIEF DESCRIPTION OF THE INVENTION

The present invention is directed to compounds of the formula

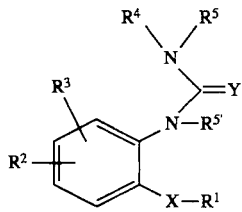

and pharmaceutically acceptable salts thereof. As used in formula I, and throughout the specification, the symbols have the following meanings:

X is a single bond, O, CO, S, NH or N(lower alkyl);

Y is O, S or NCN;

$R^1$ is alkyl, cycloalkyl, aryl, (aryl)alkyl, heterocyclo or (heterocyclo)alkyl;

$R^2$ is hydrogen, alkyl, haloalkyl, alkenyl, alkynyl, cycloalkyl, arylalkyl, (cycloalkyl)alkyl, —CN, —NO$_2$, —COR, —COOR, —CONHR, —CONR$^6$, —CF$_3$, —S—alkyl, —SO$_2$alkyl, —SO$_2$alkyl,

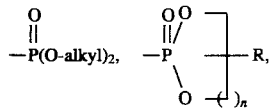

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCONR$^6$, where R is hydrogen, alkyl, haloalkyl, aryl, arylalkyl, cycloalkyl or (cycloalkyl)alkyl;

$R^3$ is hydrogen, alkyl, hydroxy, —O-alkyl, amino, substituted amino,—NHCOR,—CN or—NO$_2$;

$R^4$ is aryl, (aryl)alkyl, heterocyclo or (heterocyclo)alkyl;

$R^5$ and $R^{5'}$ are hydrogen, alkyl, (alkyl)amino, (alkyl)substituted amino or haloalkyl; or $R^4$ and $R^5$ taken together with the carbon atoms to which they are attached form a 5- to 7-membered ting which can optionally contain a O, S or NR$^7$;

$R^6$ is hydrogen, hydroxy or —OCOR;

$R^7$ is hydrogen, alkyl, aryl, arylalkyl, cycloalkyl or (cycloalkyl)alkyl; and n is an integer of 1 to 3; provided that when Y is NCN, $R^4$ is aryl or (aryl)alkyl and $R^{5'}$ is hydrogen, then $R^5$ is other than hydrogen.

The compounds of this invention possess antiischemic activity and are useful, for example as cardiovascular agents.

DESCRIPTION OF THE INVENTION

The present invention provides for compounds of formula I, pharmaceutical compositions employing such compounds and for methods of using such compounds. Listed below are definitions of various terms used to describe the compounds of the instant invention. These definitions apply to the terms as they are used throughout the specification (unless they are otherwise limited in specific instances either individually or as part of a larger group.

The term "alkyl" refers to both straight and branched chain groups having 1 to 8 carbon atoms in the normal chain, preferably 1 to 5 carbons, such as methyl, ethyl, propyl, butyl, pentyl, hexyl, heptyl, octyl, the various branched chain isomers thereof, such as isopropyl, t-butyl, isobutyl, isohexyl, 4,4-dimethylpentyl, 2,2,4-trimethylpentyl and the like as well as such groups including a halo substituent such as CCl$_3$ or CF$_3$, an alkoxy substituent, an aryl substituent, an alkylaryl substituent, a haloaryl substituent, a cycloalkyl substituent, a (cycloalkyl)alkyl substituent, a hydroxy substituent, an alkylamino substituent, an alkanoylamino substituent, an arylcarbonylamino substituent, a nitro substituent, a cyano substituent, a thiol substituent or an alkylthio substituent.

The term "alkoxy" refers to any of the above alkyl groups linked to an oxygen atom.

The term "alkylthio" refers to any of the above alkyl groups linked to a sulfur atom.

The term "alkenyl" refers to any of the above alkyl groups further containing at least one carbon to carbon double bond.

The term "alkynyl" refers to any of the above alkyl groups further containing at least one carbon to carbon triple bond.

The term "cycloalkyl" refers to saturated cyclic hydrocarbon groups containing 3 to 7 ring carbons with cyclopropyl, cyclopentyl and cyclohexyl being preferred.

The term "halogen" or "halo" refers to chlorine, bromine, iodine and fluorine.

The term "aryl" refers to phenyl, 1-naphthyl, 2-naphthyl; phenyl, 1-naphthyl, 2-naphthyl, mono-substituted with (C$_1$–C$_4$)-alkyl, (C$_1$–C$_4$)-alkylthio, (C$_1$–C$_4$)-alkoxy, halo, nitro, cyano, hydroxy, amino, (alkyl)amino, alkyl-substituted amino,—NH—(C$_1$–C$_4$)-alkyl,—N((C$_1$–C$_4$)-alkyl), —CF$_3$, —OCHF$_2$,

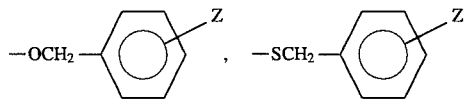

(wherein Z is hydrogen, (C$_1$–C$_4$)-alkyl, (C$_1$–C$_4$)-alkylthio, (C$_1$–C$_4$)-alkoxy, halo, hydroxy or —CF$_3$), —O—CH$_2$-cycloalkyl, or —S—CH$_2$-cycloalkyl; and phenyl, 1-naphthyl or 2-naphthyl, di-substituted with methyl, methoxy, methylthio, halo, —CF$_3$, nitro, amino or —OCHF$_2$. The term "aryl" also includes those groups listed above fused to a five- or six-membered ring which optionally contains an O, S or N atom (the nitrogen atom being substituted by an R$^7$group). Preferred aryl groups include unsubstituted phenyl and monosubstituted phenyl wherein the substituents are (C$_1$–C$_4$)-alkyl, methoxy, halo, nitro, cyano or —CF$_3$.

The term "heterocyclo" or "hetero" refers to fully saturated or unsaturated rings of 5 or 6 atoms containing one or two oxygen and/or sulfur atoms and/or one to four nitrogen atoms provided that the total number of hetero atoms in the ring is four or less. The hetero ring is attached by way of an available atom. Preferred monocyclic hetero groups include 2- and 3-thienyl, 2- and 3-furyl, 2-, 3- and 4-pyridyl and imidazolyl. The term hetero also includes bicyclic rings wherein the five or six membered ring containing oxygen, sulfur and/or nitrogen atoms as defined above is fused to a benzene ring and the bicyclic ring is attached by way of an available carbon atom. Preferred bicyclic hetero groups include 4-, 5-, 6- or 7-indolyl, 4-, 5-, 6- or 7-isoindolyl, 5-, 6-, 7-or 8-quinolinyl, 5-, 6-, 7- or 8-isoquinolinyl, 4-, 5-, 6- or 7-benzothiazolyl, 4-, 5-, 6- or 7-benzoxazolyl, 4-, 5-, 6- or 7-benzimidazolyl, 4-, 5-, 6-or 7-benzoxadiazolyl and 4-, 5-, 6- or 7-benzofuranzanyl.

The term "heterocyclo" or "hetero" also includes such monocyclic and bicyclic rings wherein an available carbon atom is substituted with a $(C_1-C_4)$-alkyl, $(C_1-C_4)$-alkylthio, $(C_1-C_4)$-alkoxy, halo, nitro, keto, cyano, hydroxy, amino, —NH—$(C_1-C_4)$-alkyl, —N $((C_1-C_4)$-alkyl$)_2$, —$CF_3$ or —$OCF_2$ or such monocyclic and bicyclic rings wherein two or three available carbons have substituents selected from methyl, methoxy, methylthio, halo, —$CF_3$, nitro, hydroxy, amino and—$OCF_2$.

The term "substituted amino" refers to a group of the formula —$NZ^1Z^2$ wherein $Z^1$ is hydrogen, alkyl, cycloalkyl, aryl, arylalkyl, (cycloalkyl)alkyl and $Z^2$ is alkyl, cycloalkyl, aryl, arylalkyl, (cycloalkyl)alkyl or $Z^1$ and $Z^2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, substituted with alkyl, alkoxy, alkylthio, halo, trifluoromethyl or hydroxy.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, or such as benzoic acid, or with organic sulfonic acids, such as $(C_1-C_4)$-alkyl- or arylsulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or m-lower alkylamine, for example ethyl-, tert-butyl-, diethyl-, diisopropyl-, triethyl-, tributyl- or dimethylpropyl-amine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in diastereomeric forms or in mixtures thereof. The above described processes can utilize racemates, enantiomers or diastereomers as starting materials. When diastereomeric products are prepared, they can be separated by conventional methods for example chromatographic or fractional crystallization. Preferred compounds are those with the 3S or 4R stereochemistry.

It should be understood that the present invention includes prodrug forms of the compounds of formula I such as alkylesters of acids.

The compounds of the instant invention may, for example, be in the free or hydrate form, and may be obtained by methods exemplified by the following descriptions.

Compounds of formula I wherein Y is oxygen or sulfur and $R^4$ is hydrogen, can be prepared by reacting amine of formula

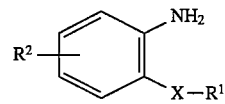

with an isocyanate (where Y is O ) or isothiocyanate (where Y is S) of formula

in the presence of a base such as triethyl amine, pyridine and sodium hydride.

Compounds of formula I wherein Y is oxygen or sulfur can also be prepared by first reacting the amine of formula II with a compound of formula

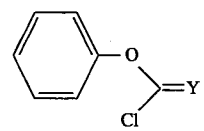

to provide an intermediate of formula

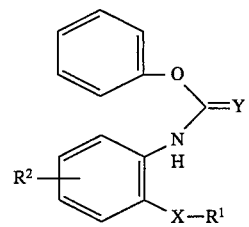

which can be further reacted with an amine of formula

Compounds of formula I wherein Y is oxygen or sulfur can also be prepared by reacting an amine of formula VI with a chloroformate (where Y is O) or chlorothionoformate (where Y is S) of formula IV to provide an intermediate of formula

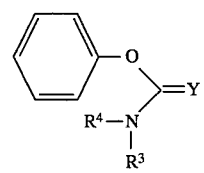

which can then be reacted with an amine of formula II in the presence of a base such as triethylamine, pyridine and sodium hydride.

Compounds of formula I wherein Y is NCN can be prepared by treatment of a compound of formula I wherein Y is sulfur with cyanamide in the presence of a carbodiimide such as dicyclohexylcarbodiimide and an amine such as triethylamine.

Compounds of formula I wherein Y is NCN can also be prepared by first reacting an amine of formula II with diphenylcyanocarbonimidate to provide an intermediate of formula

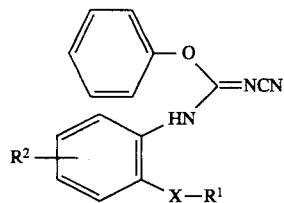
VII which can be further reacted with an amine of formula VI in the presence of a base such as triethyl amine and sodium hydride or a Lewis acid such as trimethylaluminum.

Compounds of formula I wherein Y is NCN can also be prepared by treatment of a compound of formula VI with diphenylcarbonimidate to provide an intermediate of formula

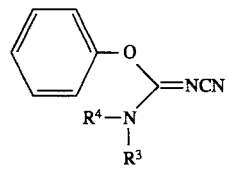
IX which can be further reacted with an amine of formula II in the presence of a base such as triethylamine and sodium hydride or a Lewis acid such as trimethylaluminum.

Amine of formula II wherein X is a single bond, $R^2$ is cyano, can be prepared according to Schemes A and B, below. Other compounds of formula II wherein X is a single bond and $R^2$ is other than cyano (e.g., nitro, $CF_3$, halo etc., S-alkyl, O-alkyl) can be prepared by slight modification of Schemes A and B.

SCHEME A

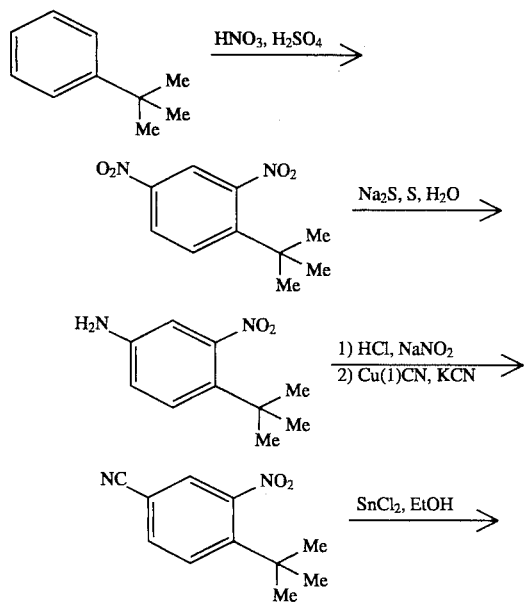

SCHEME A -continued

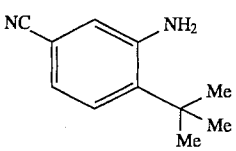

SCHEME B

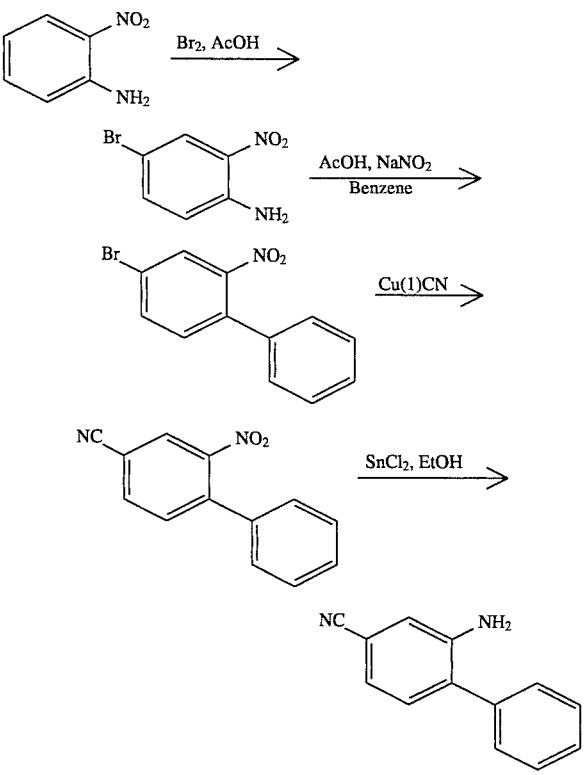

Compounds of formula II wherein X is oxygen and $R^2$ is cyano can be prepared according to schemes C and D. Compounds of formula II wherein X is oxygen, sulfur, NH, N(lower alkyl) or CO and $R^2$ is other than cyano, can be prepared by modification of scheme C. Compounds of formula II wherein X is sulfur, NH, N(lower alkyl) or CO and $R^2$ is cyano, can be prepared by modification of scheme C.

SCHEME C

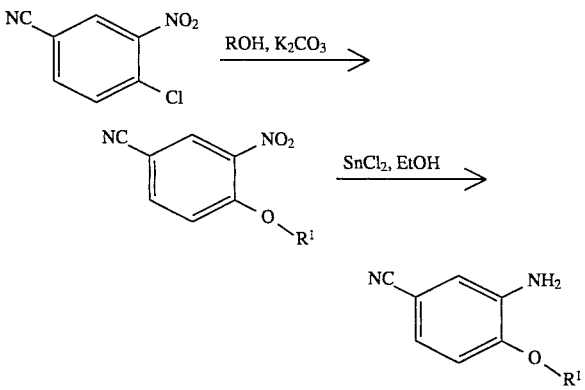
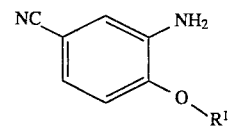

SCHEME D

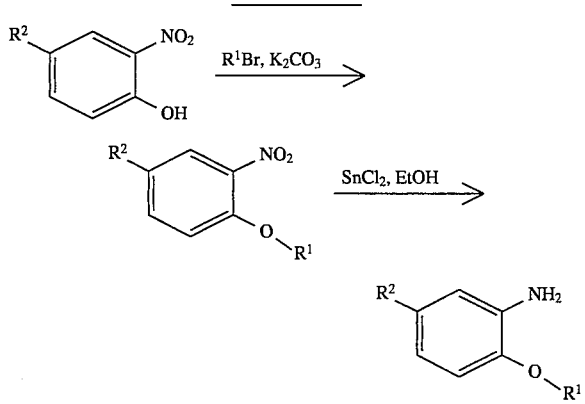

Compounds of formula III, IV and VI are commercially available.

The compounds of the present invention and any one of the R's can have asymmetric carbons. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

Compounds of formula I, wherein $R^5$ and $R^{5'}$ are hydrogen can exist as tautomers I', I" and I'''. All of the tautomeric forms are included in the scope of this invention.

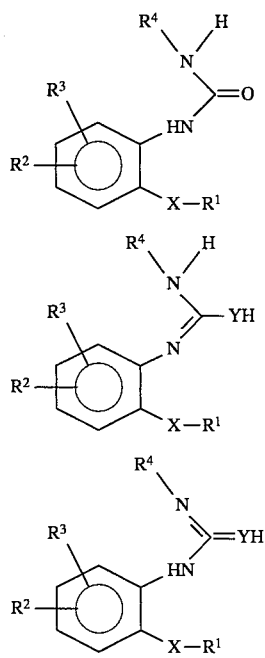

The preferred compounds of the present invention are those compounds of formula I where:

X is a single bond, O or S;

Y is —O— or NCN;

$R^1$ is t-butyl, cycloalkyl or aryl;

$R^2$ is hydrogen, CN, $NO_2$, $CONH_2$, $CF_3$ or halo;

$R^3$ is hydrogen; and $R^4$ is aryl or heterocyclo.

Compounds of formula I may be used as antiischemic agents, i.e., for the treatment of ischemic conditions such as myocardial ischemia, cerebral ischemia, lower limb ischemia and the like.

Thus a composition containing one (or a combination) of the compounds of this invention, may be administered to a species of mammal (e.g., humans) suffering from an ischemic or hypertensive condition.

A single dose, or two to four divided daily doses, provided on a basis of about 0.00 1 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the potassium channel activating activity of compounds of this invention, these compounds are also useful in the treatment of cardiovascular disorders and any disorders associated with smooth muscle contraction. For example, compounds of the present invention are useful as therapy for congestive heart failure, therapy for peripheral vascular disorders (e.g. Raynaud's Disease), therapy for pulmonary hypertension, as anti-anginal agents, as anti-fibrillatory agents and in limiting myocardial infarction.

Compounds of the present invention are additionally expected to be useful in the treatment of central nervous system disorders (e.g., Parkinsonism, as anti-tremor agents, epilepsy), in therapy for renal failure, in therapy for urinary incontinence, as anti-diarrheal agents, in therapy for pre-eclampsia, dysmenorrhea and premature labor, for the treatment of male impotence, as well as for the promotion of hair growth (e.g., in the treatment of male pattern baldness) and as anti-asthmatic agents.

The compounds of this invention can also be formulated in combination with a diuretic such as chlorothiazide, hydrochlorothiazide, flumethiazide, hydroflumethiazide, bendroflumethiazide, methylchlothiazide. trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin convening enzyme inhibitors such as captopril, zofenopfil, fosinopril, enalapfil, ceranopril, cilazopfil, delapfil, pentopfil, quinapfil, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the rang indicated is obtained.

The following examples and preparations describe the manner and process of making and using the invention and

EXAMPLE 1

N-[5-Cyano-2-(1,1-dimethylethyl)phenyl]N'-(phenylmethyl) urea

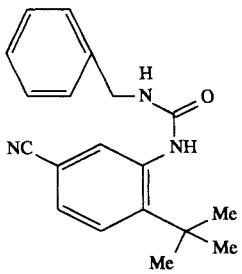

A. (1,1-Dimethylethyl)-2,4-dinitrobenzene

To a mixture of concentrated sulfuric acid (50 mL) and 70% nitric acid (40 mL) at 45° C. was added ter-butylbenzene (30.0 g, 0.22 mol) over the course of 30 minutes (the addition was moderately exothermic). The reaction mixture was stirred for 45 minutes upon completion of the addition and transferred to a separatory funnel. The organic phase was separated and the acid fraction was diluted with ice water and extracted with ethyl acetate. The organic fractions were combined and washed with water, 1N sodium hydroxide and saturated sodium chloride solution. The extract was dried over magnesium sulfate and evaporated in vacuo to obtain a yellow solid (42 g). The crude material was triturated with cold ethanol to afford the title compound (34.6 g, 70%) as a pale yellow solid, mp 60°–62° C. Analysis calculated for $C_{10}H_{12}N_2O_4$: C, 53.57; H, 5.39; N, 12.49. Found: C, 53.70; H, 5.41; N, 12.22.

B. 1-Amino-4-(1,1-dimethylethyl)-3-nitrobenzene

To a slurry of title A compound (20.0 g, 89 mmol) in water (112 mL) at 100° C. was added (over 1.25 hours) a solution of sodium sulfide.9H$_2$O (42.8 g) and sulfur (5.70 g) dissolved in distilled water (67 mL). The reaction mixture was heated for 1.5 hours at 100° C. and cooled to room temperature. The reaction mixture was partitioned between diethyl ether and distilled water. The organic phase was washed with saturated sodium chloride solution, dried over magnesium sulfate and evaporated in vacuo to obtain an orange gum (18 g). The crude material was chromatographed on silica gel eluting with 3:1 hexane/ethyl acetate to obtain the desired product (14.8 g, 86% ) as an orange oil which slowly crystallized on standing, mp 57°–58° C. Analysis calculated for $C_{10}H_{14}N_2O_2$: C, 61.84; H, 7.26; N, 14.42. Found: C, 61.97; H, 7.19; N, 14.14.

C 4-(1,1-Dimethylethyl)-3-nitro-benzonitrile

To a solution of title B compound (10.0 g, 51.5 mmol) in ethanol (50 mL) at 0° C. was added a solution of concentrated hydrochloric acid (12.5 mL) in ethanol (87.5 mL) followed by a solution of sodium nitrite (3.91 g, 56.6 mmol) in distilled water (25 mL). The reaction mixture was stirred at 0° C. for ten minutes and added in portions to a solution of copper(1)cyanide (18.45 g) and potassium cyanide (13.41 g) in distilled water (200 mL) at 100° C. The reaction mixture was stirred an additional 15 minutes at 100° C., cooled to room temperature, and partitioned between distilled water and ethyl acetate. The organic fraction was washed with saturated sodium chloride solution, dried over magnesium sulfate and evaporated in vacuo to obtain an orange gum (8.20 g). The crude product was purified by chromatography on silica gel eluting with 9:1 hexane/ethyl acetate to afford the title compound (3.74 g, 42%) as a yellow solid, mp 67-69° C. Analysis calculated for $C_{11}H_{12}N_2O_2$: C, 4.69; H, 5.92; N, 13.72. Found: C, 64.60; H, 5.94; N, 13.51

D 3-Amino-4-(1,1-dimethylethyl)benzonitrile

A mixture of title C compound (3.74 g, 18.3 mmol) and stannous chloride dihydrate (20.6 g, 91.6 mmol) in ethanol (25 mL) was heated at reflux for 45 minutes. The reaction mixture was poured onto ice and neutralized with solid sodium bicarbonate. The pH was adjusted to ca. 12 with 50% NaOH solution and the reaction mixture was extracted with diethyl ether. The extracts were washed with saturated sodium chloride solution, dried over magnesium sulfate and evaporated in vacuo to obtain the desired compound (3.20 g, 100%) as a brown solid. The crude product was used in the next step without further purification.

E. N-[5-Cyano-2-(1,1-dimethylethyl)phenyl]- N'-(phenylmethyl)-urea

A solution of title D compound (0.40 g, 2.29 mmol) and benzyl isocyanate (0.31 g, 2.29 mmol) in chloroform (4 mL) was heated at reflux for 12 hours. The solvent was recovered under vacuum and the residue was chromatographed on silica eluting with hexane/ethyl acetate (3:2) to obtain the title compound (0.49 g, 70%) as an off-white solid, mp 160°–161° C. Analysis calculated for $C_{19}H_{21}N_3O$: C, 74.24; H, 6.89; N, 13.67. Found: C, 74.02; H, 6.85; N, 13.82.

EXAMPLE 2

N-[5-Cyano-2-(1,1-dimethylethyl)phenyl]-N'-phenylurea

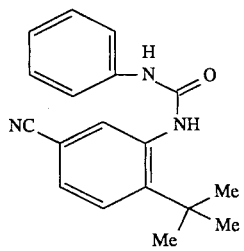

A solution of 3-amino-4-(1,1-dimethylethyl)benzonitrile (0.40 g, 2.29 mmol; the title D compound of Example 1) and phenyl isocyanate (0.27 g, 2.29 mmol) in chloroform (4 mL) was heated at reflux for 16 hours. The solvent was recovered under vacuum and the residue was triturated to obtain the title compound (0.58 g, 86%) as an off-white solid. The partially purified product was crystallized from isopropanol to obtain an off-white solid (0.46 g), mp 225°–226° C. Analysis calculated for $C_{18}H_{19}N_3O \cdot 0.19H_2O$: C, 72.83; H, 6.58; N, 14.16. Found: C, 73.04; H, 6.52; N, 13.95.

EXAMPLE 3

N-[5-Cyano-2-(1,1-dimethylethyl)phenyl]-N'-(3-pyridinyl)urea

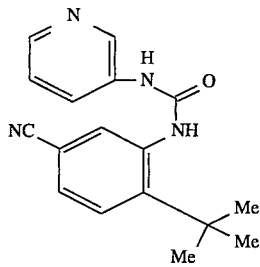

A solution of 3-amino-4-(1,1-dimethylethyl)benzonitrile (0.50 g, 2.87 mmol; the title D compound of Example 1) and nicotinyl azide (0.27 g, 3.58 mmol) in toluene (10 mL) was heated at 85° C. for three hours. The solvent was recovered under vacuum and the residue was crystallized from ethyl acetate/isopropanol/hexane to obtain the title compound as an off-white solid (0.50 g, 59%), mp 194°–196° C. Analysis calculated for $C_{17}H_{18}N_4O.0.43H_2O$: C., 67.60; H, 6.29; N, 18.55. Found: C, 68.05; H, 6.24; N, 18.10.

EXAMPLE 4

N''-Cyano-N- [5-cyano-2-(1,1-dimethylethyl)phenyl]- N'-phenylguanidine

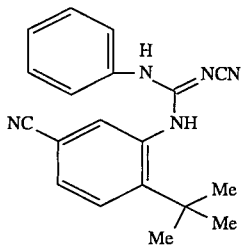

A. N-[5-Cyano-2-(1,1-dimethylethyl)phenyl]-N'-(phenylmethyl)-thiourea

To a solution of 3-amino-4-(1,1-dimethylethyl)benzonitrile (0.60 g, 3.44 mmol: the title D compound of Example 1) and phenyl isothiocyanate (0.51 g, 3.79 mmol) in dry tetrahydrofuran (6 mL) cooled to 0° C. was added sodium hydride (60% dispersion in mineral oil, 0.15 g, 3.77 mmol). The reaction was heated at reflux for two hours and quenched by the addition of distilled water. The phases were separated and the aqueous phase was extracted with ethyl acetate. The combined organic phases were washed with saturated sodium chloride solution and dried over magnesium sulfate. The solvent was recovered under vacuum to obtain a brown gum. The crude material was chromatographed on silica eluting with hexane/ethyl acetate (3:1) to obtain partially purified material (0.58 g) as a yellow foam.

B. N''-Cyano-N -[5-cyano-2-(1,1-dimethylethyl)phenyl]-N'-phenyl-guanidine

A solution of title A compound (0.55 g, 1.8 mmol), cyanamide (0.11 g, 2.67 mmol), dicyclohexylcarbodiimide (0.73 g, 3.56 mmol) and triethylamine (12 mg) in N,N-dimethylformamide (2.75 mL) was stirred at room temperature for 18 hours. The reaction mixture was partitioned between ethyl acetate and 10% citric acid solution. The organic fraction was washed with distilled water, saturated sodium chloride solution and dried over magnesium sulfate. The solvent was recovered under vacuum to obtain a brown gum. The crude material was partially purified by chromatography on silica gel eluting with hexane/ethyl acetate (2:1) to obtain a white foam (0.53 g) which was further purified by reverse phase preparative HPLC to provide the title compound (0.12 g) as a white solid, mp 194°–196° C. Analysis calculated for $C_{19}H_{19}N_5.0.26H_2O$: C, 70.85; H, 6.11; N, 21.74. Found: C, 71.15; H, 6.00; N, 21.44.

EXAMPLE 5

N''-Cyano-N-[5-cyano-2-(1,1-dimethylethyl)phenyl]-N'-(3-pyridinyl)guanidine

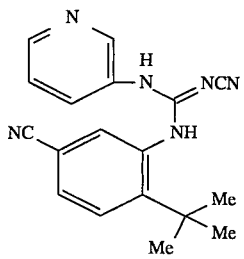

A. 3-[((Cyanoimino)phenoxymethyl)amino]-4-(1,1-dimethyl-ethyl)benzonitrile

To a solution of 3-amino-4-(1,1-dimethylethyl)benzonitrile (0.25 g, 1.43 mmol; the title D compound of Example 1) in dry tetrahydrofuran (5 mL) was added sodium hydride (60% dispersion, 91 mg, 2.3 mmol). After stirring at room temperature for 15 minutes, diphenylcyanocarbonimidate (0.51 g, 2.15 mmol) was added. The reaction mixture was heated at reflux for four hours and quenched by the addition of saturated ammonium chloride solution. The layers were separated and the aqueous layer was extracted with ethyl acetate. The combined organic layers were washed with saturated sodium bicarbonate solution, saturated sodium chloride solution, dried over magnesium sulfate and evaporated in vacuo to obtain a brown gum (0.89 g). The crude material was purified by chromatography on silica gel eluting with hexane/ethyl acetate (7:3) to obtain the title compound (0.35 g, 77%) as a pale green solid, mp 179°–181° C.

B. N''-Cyano-N -[5-cyano-2-(1,1-dimethylethyl)phenyl]-N'-(3-pyridinyl)guanidine

A solution of title A compound (0.40 g, 1.26 mmol) and 3-aminopyridine (0.14 g, 1.51 mmol) in N,N-dimethylformamide (8 mL) was heated under argon at 100° C. for four hours. The reaction mixture was partitioned between distilled water and ethyl acetate. The organic phase was washed with distilled water, saturated sodium chloride solution, dried over magnesium sulfate and evaporated under vacuum to obtain a brown gum. The crude material was purified by chromatography on silica gel eluting with hexane/ethyl acetate (7:3) to give a pale yellow solid which was crystallized from isopropanol to give an off-white solid (0.23 g, 58%), mp 219°–221° C. Analysis calculated for $C_{18}H_{18}N_6.0.30C_3H_8O$: C, 67.48; H, 6.11; N, 24.98. Found: C, 67.47; H, 5.87; N, 24.93.

EXAMPLE 6

N-[(4-Chloro-3-pyridinyl)-N'-[5-cyano-2-(1,1-dimethylethyl)-phenyl]urea

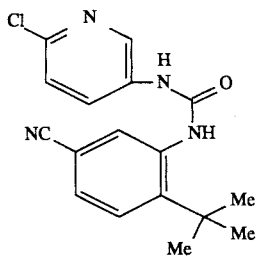

A. 3-(Phenoxycarbonyl)amino-4-(1,1-dimethylethyl)-benzonitrile

To a solution of 3-amino-4-(1,1-dimethylethyl)benzonitrile (1.5 g, 8.61 mmol; the title D compound of Example 1) in methylene chloride (15 mL) containing pyridine (0.85 g, 10.76 mmol) cooled to 0° C. was added phenyl chloroformate (1.42 g, 9.0 mmol). The reaction mixture was stirred for one hour at ambient temperature, then partitioned between ethyl acetate and 1N hydrochloric acid solution. The organic phase was washed with saturated sodium bicarbonate solution, saturated sodium chloride solution and dried over magnesium sulfate. The solvent was recovered under vacuum to obtain a red gum. The crude product was purified by chromatography on silica gel eluting with hexane/ethyl acetate (4:1) to afford the desired compound as a gummy white solid (2.38 g, 94%).

B. N-[(4-Chloro-3-pyridinyl)-N'-[5-cyano-2-(1,1-dimethylethyl)-phenyl]urea

A solution of title A compound (0.60 g, 2.04 mmol) and 5-amino-2-chloropyridine (0.29 g, 2.24 mmol) in N,N-dimethylformamide (6 mL) containing N,N-dimethylaminopyridine (50 mg) was heated at 100° C. for 45 minutes. The reaction mixture was partitioned between ethyl acetate and saturated sodium bicarbonate solution. The organic phase was washed with saturated sodium bicarbonate solution, saturated sodium chloride solution, dried over magnesium sulfate and evaporated in vacuo to obtain a pink solid. The crude material was purified by chromatography on silica gel eluting with ethyl acetate/hexane (2:1) to obtain a colorless solid (0.63 g, 73%) mp 233°–234° C. Analysis calculated for $C_{17}H_{17}N_4OCl.0.12H_2O$: C, 61.71; H, 5.25; N, 16.93; Cl, 10.71. Found: C, 61.93; H, 5.06; N, 16.71; Cl, 10.53.

EXAMPLE 7

N-[5-Cyano-2-(1,1-dimethylethyl)phenyl]-N'-[1,3-dihydro-2-(phenylmethyl)-2H-isoindol-5-yl]urea

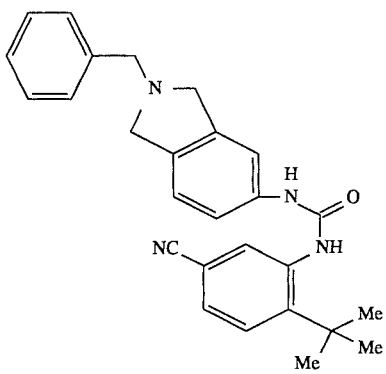

A. 2,3-Dihydro-5-nitro-2-(phenylmethyl)]-1H-isoindole

The title compound was prepared according to the procedure described in U.S. Pat. No. 5,026,856, issued in 1991 to T. Yatsunami et al.

B. 5-Amino-2,3-dihydro-2-(phenylmethyl)]-1H-isoindole

A suspension of title A compound (2.0 g, 7.8 mmol) in ethanol (50 mL) was treated with stannous chloride hydrate (8.8 g, 38.0 mmol) at room temperature and the reaction mixture was stirred for four hours. The reaction mixture was concentrated in vacuo, basified with saturated potassium carbonate solution, diluted with ethyl acetate (200 mL) and filtered through celite. The two layers were separated and aqueous layer was extracted with ethyl acetate one more time. The combined extracts were washed with brine (100 mL), dried over anhydrous magnesium sulfate and evaporated. The residue was triturated with isopropyl ether to give the title compound (1.3 g, 74%) as a brown solid, mp 110°–115° C.

C. N-[5-Cyano-2-(1,1-dimethylethyl)phenyl]-N'-[1,3-dihydro- 2(phenylmethyl)-2H-isoindol-5-yl]urea The title compound was prepared from 3-(phenoxycarbonyl)amino-4-( 1,1-dimethylethyl)-benzonitrile (0.35 g, 1.19 mmol; the title A compound of Example 6) and 5-amino-2, 3-dihydro-2-(phenylmethyl)]-1H-isoindole (0.28 g, 1.25 mmol; the title B compound) by the same procedure as described in Example 6, part B. The crude material was purified by chromatography on silica gel eluting with 2.5% methanol in ethyl acetate to obtain an off-whim foam which was triturated with isopropyl ether to provide the title compound (0.34 g, 63%) as an off-white solid, mp 185°–187° C. Analysis calculated for $C_{27}H_{28}N_4O.0.37 H_2O$: C, 75.22; H, 6.72; N, 12.99. Found: C, 75.59; H, 6.70; N, 12.62.

EXAMPLE 8

N-[5-Cyano-2-(1,1-dimethylethyl)phenyl]-N'-[3-[[methyl-(phenylmethyl)amino]methyl]phenyl]urea

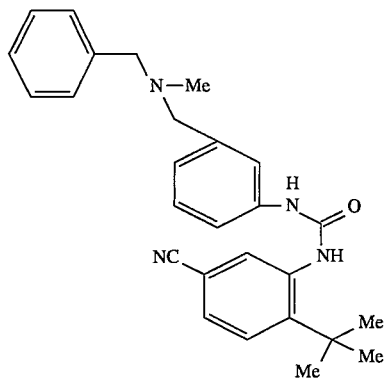

The title compound was prepared from 3-(phenoxycarbonyl)amino-4-(1,1-dimethylethyl)-benzonitrile (the title A compound of Example 6) by the same procedure as described in Example 6, part B. The crude material was crystallized from hexane/ethyl acetate to afford the title compound (0.48 g, 66%) as a white solid, mp 154°–156° C. Analysis calculated for $C_{27}H_{30}N_4O \cdot 0.16H_2O$: C, 75.52; H, 7.12; N, 13.05. Found: C, 75.56; H, 7.10; N; 13.01.

EXAMPLE 9

N-4-Chlorophenyl-N-2-(dimethylamino)ethyl-N'[5-cyano-2-(1,1-dimethylethyl)phenyl]urea

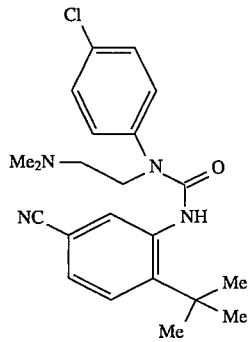

A. 4-Chloro-N -[(2-dimethylamino)ethyl]aniline

To an ice cold reaction mixture containing 4-chloroaniline (1.28 g, 10.0 mmol) and 2-dimethylaminoethyl chloride (6 mL of a 2M solution in toluene) in dimethylformamide (5.0 mL) under argon was added sodium hydride (515 mg of 60% dispersion, 13.0 mmol). The cooling bath was removed and the reaction was stirred at room temperature for two hours. The reaction mixture was heated at 65° C. for 16 hours. The reaction mixture was allowed to cool to ambient temperature and carefully diluted with water. It was extracted with ethyl acetate; ethyl acetate extracts were washed with water and dried over magnesium sulfate. The solvent was evaporated to yield a brown oil. This material was combined with another batch of the same product and purified by flash chromatography on silica gel (10% methanol in dichloromethane) to yield the title compound as a yellow oil.

B. N-4-Chlorophenyl-N -2-(dimethylamino)ethyl-N'[5-cyano- 2(1,1-dimethylethyl)phenyl]urea The title compound was prepared from 4-chloro—N -[(2-dimethylamino)ethyl]aniline (the title A compound) and 3-(phenoxycarbonyl)amino-4-(1,1-dimethylethyl)-benzonitrile (the title A compound of Example 6) by the same procedure as described in Example 6, part B. The crude material was chromatographed on silica eluting with methylene chloride/methanol (9:1) to obtain an amber gum (0.38 g, 70%) which was triturated with isopropyl ether to obtain a white solid, mp 93°–95° C. Analysis calculated for $C_{22}H_{27}N_4OCl \cdot 0.12H_2O$: C, 65.87; H, 6.85; N, 13.97; Cl, 8.84. Found: C. 66.28; H, 6.80; N, 13.56; Cl, 8.89.

EXAMPLE 10

N-[5-Cyano-2-(1,1-dimethylethyl)phenyl]-N'-(5-pyrimidinyl) urea

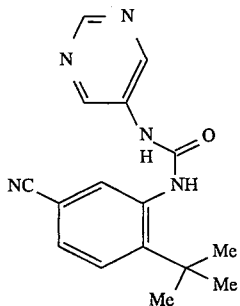

The title compound was prepared from 3-(phenoxycarbonyl)amino-4-(1,1-dimethylethyl)-benzonitrile (the title A compound of Example 6) and 5-aminopyrimidine by the same procedure as described in Example 6, part B. The crude material was purified by chromatography on silica gel 0 eluting with 5% methanol in ethyl acetate to obtain the title compound (0.35 g, 86%) of as a white solid, mp 208°–209° C. Analysis calculated for $C_{16}H_{17}N_5O$: C, 65.07; H, 5.80; N, 23.71. Found: C, 64.92; H, 5.88; N, 23.76.

EXAMPLE 11

N-[5-Cyano-2-(1,1-dimethylethyl)phenyl]-N'-(2-pyrazinyl)-urea

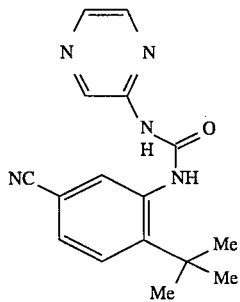

The tide compound was prepared from 3-(phenoxycarbonyl)amino-4-(1,1-dimethylethyl)-benzonitrile (the tide A compound of Example 6) and aminopyrazine by the same procedure as described in Example 6, part B. The crude material was purified by chromatography on silica gel eluting with 2% methanol in ethyl acetate to obtain the title compound (0.25 g, 50%) as an off-white solid, mp 203°–205° C. Analysis calculated for $C_{16}H_{17}N_5O \cdot 0.03C_4H_8O_2$: C, 64.82; H, 5.88; N, 23.16. Found: C, 65.14; H, 5.85; N, 22.85.

EXAMPLE 12

N-[5-Cyano-2-(1,1-dimethylethyl)phenyl]-
N'-(4-pyridinyl)urea

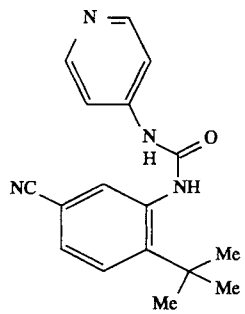

The title compound was prepared from 3-(phenoxycarbonyl)amino-4-(1,1-dimethylethyl)-benzonitrile (the title A compound of Example 6) and 4-aminopyridine by the same procedure as described in Example 6, part B. The crude material was purified by chromatography on silica gel eluting with 7.5% methanol in methylene chloride to obtain the title compound (278 mg) as an amorphous white solid, mp 125°–130° C. Analysis calculated for $C_{17}H_{18}N_4O$·1.20$H_2O$: C, 64.61; H, 6.51; N, 17.73. Found: C, 64.66; H, 6.07; N, 17.68.

EXAMPLE 13

N-[5-Cyano-2-(1,1-dimethylethyl)phenyl]-
N'-(2-pyridinyl)urea

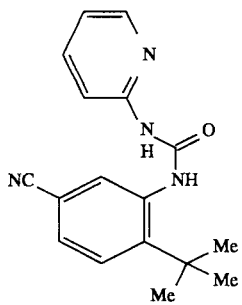

The title compound was prepared from 3-(phenoxycarbonyl)amino-4-(1,1-dimethylethyl)-benzonitrile (the title A compound of Example 6) and 2-aminopyridine by the same procedure as described in Example 6, part B. The crude material was purified by chromatography on silica gel eluting with ethyl acetate/hexane (1:1) to obtain the title compound (0.36 g, 77%) as an off-white solid. mp 198°–200° C. Analysis calculated for $C_{17}H_{18}N_4O$·0.20$C_4H_8O_2$: C, 68.53; H, 6.33; N, 17.96. Found: C. 68.52; H, 6.26; N, 17.93.

EXAMPLE 14

N-[4-Cyano-(1,1'-biphenyl)-2-yl]-N'-(3-pyridinyl)urea

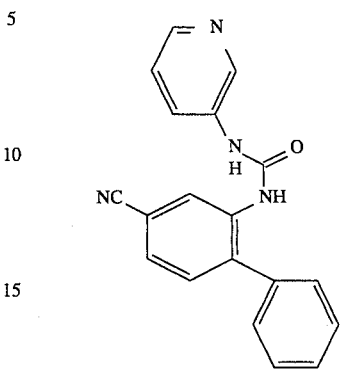

A. 4-Bromo-2-nitroaniline

To a solution of 2-nitroaniline (10.0 g, 72.4 mmol) and sodium acetate (10 g) dissolved in glacial acetic acid (100 mL) cooled to 0° C. was added bromine (11.8 g) dissolved in glacial acetic acid (20 mL). The reaction mixture was stirred at room temperature for one hour and poured into distilled water (800 mL). The precipitate was collected by suction filtration and crystallized from ethanol to obtain the title compound (10.7 g, 68%) as an orange solid.

B. 4-Bromo-2-nitrobiphenyl

To a solution of title A compound (10.68 g, 49.2 mmol) dissolved in a mixture of glacial acetic acid (100 mL) and distilled water (66 mL) cooled to 0° C. was added an aqueous solution of sodium nitrite (3.74 g, 54.1 mmol, dissolved in 47 mL distilled water) over a period of 15 minutes. After stirring an additional 10 minutes at 0° C., benzene (133.5 mL) and sodium acetate were added and the reaction mixture was stirred 48 hours at room temperature. The reaction mass was transferred to a separatory funnel and the organic fraction was separated and set aside. The aqueous layer was returned to the reaction flask and fresh benzene (300 mL) was added. The reaction mixture was stirred an additional 24 hours at a room temperature. The organic layer was separated and the combined organics were washed with saturated sodium chloride solution and dried over magnesium sulfate. The solvent was removed and the residue was azeotroped with heptane to obtain a dark brown solid (12.2 g). The crude product was chromatographed on silica eluting with 15% ethyl acetate in hexane to afford the title compound as an orange gum (5.17 g, 38%).

C. 4-Cyano-2-nitrobiphenyl

A solution of title B compound (4.56 g, 16.4 mmol) and copper (I) cyanide (2.94 g, 32.8 mmol) in N-methylpyrrolidone (45 mL) was heated at 175°–180° C. for 2.5 hours. The reaction mixture was cooled to room temperature and diluted with a large excess of diethyl ether. The precipitated solids were filtered and the filtrate was washed with distilled water, 1N hydrochloric acid, saturated sodium bicarbonate solution and brine. The extract was dried over magnesium sulfate and evaporated in vacuo. The crude material was chromatographed on silica eluting with hexane/ethyl acetate (4:1) to obtain the title compound (2.08 g) as a pale yellow solid.

D. 2-Amino-4-cyanobiphenyl

A mixture of title C compound (1.82 g, 8.12 mmol) and stannous chloride dihydrate (9.16 g, 40.6 mmol) in ethanol (20 mL) was heated at reflux for 5 minutes. The reaction mixture was poured onto ice/water and neutralized with solid sodium bicarbonate. The pH was adjusted to 12 with sodium hydroxide solution and the aqueous mixture was extracted with ethyl acetate. The extract was washed with saturated sodium chloride solution and dried over magnesium sulfate. The solvent was recovered in vacuo to obtain a yellow gum which was triturated with cold pentane to obtain the tire compound as an off-white solid (1.40 g ).

E. N-[4-Cyano-(1,1'-biphenyl)-2-yl]-N'-(3-pyridinyl)urea

A solution of title D compound (0.30 g, 1.54 mmol) and nicotinyl azide (0.29 g, 1.84 mmol) in toluene (5 mL) was heated at 85° C. for 1.5 hours. The solvent was recovered under vacuum and the residue was triturated with isopropyl ether to obtain the crude product (0.48 g) which was crystallized from isopropanol to obtain the title compound (0.36 g) as an off- white solid, mp 180°–182° C. Analysis calculated for $C_{19}H_{14}N_4O.0.07H_2O$: C, 72.30; H, 4.52; N, 17.75. Found: C, 72.19; H, 4.40; N, 17.86

EXAMPLE 15

N-(5-Cyano-2-phenoxyphenyl)-N'-(3-pyridinyl)urea

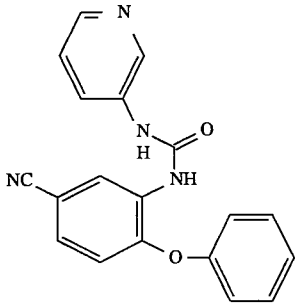

A. 3-Nitro-4-phenoxybenzonitrile

To a solution of 4-chloro-3-nitrobenzonitrile (3.6 g, 20 mmol) and phenol (2.8 g, 30 mmol) in dimethylformamide (75 mL) was added solid potassium carbonate (5 g, 36 mmol). The suspension was stirred at room temperature under argon for eight hours and heated at 50 ° C. for 18 hours. The reaction mixture was concentrated in vacuo and the residue was dissolved in water (500 mL). The aqueous layer was extracted with ethyl acetate (2×250 mL); combined extracts were washed with sainted potassium carbonate and dried over magnesium sulfate. The solvent was evaporated and the residue was purified by flash column chromatography to give an oil which solidified upon standing.

B. 3-Amino-4-phenoxybenzonitrile

To a solution of title A compound (3.0 g, 12.5 mmol) in ethyl acetate (125 mL) at room temperature was added stannous chloride dihydrate (9.0 g, 40 mmol). The reaction mixture was stirred at room temperature under argon for four hours. It was treated with 10 mL of saturated potassium carbonate at 0° C. and stirred for two hours before solid potassium carbonate was added to give a white suspension. The suspension was filtered through a pad of celite and the filtrate was concentrated in vacuo to give a white solid (2.3 g, 88%).

C. N-(5-Cyano-2-phenoxyphenyl)-N'-(3-pyridinyl)urea

A solution of title B compound (320 mg, 1.52 mmol) and nicotinyl azide (270 mg, 1.83 mmol) in 3 mL of toluene was heated at 95° C. under argon for three hours. The reaction mixture was cooled to room temperature and the white precipitate was collected by filtration. The solid collected was recrystallized from ethyl acetate-methanol-hexanes to give a white powder (350 mg, 70%), mp 208°–209° C. Analysis calculated for $C_{19}H_{14}N_4O_2$. 0.09 $H_2O$:C, 68.74; H,4.31; N,16.87. Found: C, 68.76; H, 4.21; N, 16.85.

EXAMPLE 16

N-[2-(1- Methylethoxy)-5-nitrophenyl]-N'-(3-pyridinyl)urea

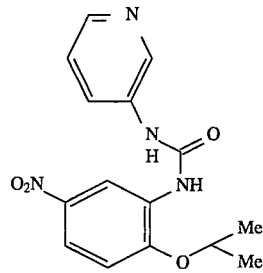

A. 2-(1-Methylethoxy)-5-nitrobenzaldehyde

A mixture of 2-hydroxy-5-nitrobenzaldehyde (24.80 g, 148.40 mmol) and cesium carbonate (72.5 g, 222.49 mmol) in dimethylformamide (100 mL) was treated with iso-propyl iodide (30 mL, 296.79 mmol) and stirred at room temperature for six days. The reaction mixture was partitioned between ethyl acetate (1000 mL)/water (600 mL) and shaken well. The organic layer was removed, washed with water (3×400 mL), brine (2×300 mL) and dried over magnesium sulfate. The solvent was removed and the residue was triturated with hexanes to give the title product (27.14 g, 87%) as a pale yellow solid, mp 91°–92 ° C. Analysis calculated for $C_{10}H_{11}NO_4$: C, 57.41; H, 5.30; N, 6.70. Found: C, 57.43; H, 5.30; N, 6.68.

B. 2-(1-Methylethoxy)-5-nitrobenzoic acid

A solution of title A compound (6.50 g, 31.07 mmol) in acetone (20 mL) was treated with a 2.5M solution of Jones' reagent (18.6 mL, 46.61 mmol) and stirred at room temperature for 30 minutes. The reaction mixture was partitioned between ethyl acetate and water. The organic layer was separated, washed with water (until the aqueous layer was no longer orange/yellow), brine (100 mL) and dried over magnesium sulfate. The solvent was removed to give the title product (6.01 g, 86%) as a pale yellow solid, mp 124°–125 ° C. Analysis calculated for $C_{10}H_{11}NO_5$: C, 3.33; H, 4.92; N, 6.22. Found: C, 53.30; H, 4.80; N, 6.07.

C. N-[2-(1-Methylethoxy)-5-nitrophenyl]-N'-(3-pyridinyl)urea

A solution of title B compound (2.75 g, 12.20 mmol) in dimethyl-formamide (9 mL) and triethylamine (1.70 mL, 12.20 mmol) was cooled in an ice/water bath and treated with diphenylphosphoryl azide (2.63 mL, 12.20 mmol). The reaction was allowed to warm to room temperature and stirred for two hours. The mixture was partitioned between ethyl acetate and saturated sodium bicarbonate. The organic layer was washed with water, brine and dried over magnesium sulfate. The solvent was removed to give a semi-solid which was triturated with hexanes containing a small amount of dichloromethane. The solid was filtered off and the filtrate was concentrated to afford a clear yellow oil (2.89 g, 95%). A portion (229 mg, 0.915 mmol) of this product in toluene (6 mL) was heated at 70° C. under argon for 45 minutes. The reaction mixture was allowed to cool to room temperature and treated with a solution of 3-aminopyridine (86 mg, 0.915 mmol) in dichloromethane (1 mL). The resulting solid was dissolved by the addition of methanol, preabsorbed onto silica gel and purified by flash chromatography on silica gel (100% ethyl acetate) to afford the title product (136 mg, 47%) as a yellow solid, mp 231-232 ° C. Analysis calculated for C15H16N4O4: C, 56.96; H, 5.10; N, 17.71. Found: C, 57.31; H, 5.18; N, 17.52.

EXAMPLE 17

4-(1,1-Dimethylethyl)-2-[[[(3-pyridinyl)amino]carbonyl]-amino]benzamide

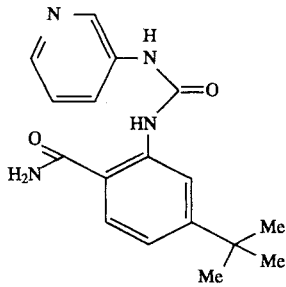

A. 1-Bromo-4-(1,1-dimethylethyl)-2-nitrobenzene

To a mixture of nitric acid (70%, 7.45 mL) and concentrated sulfuric acid (9.31 mL) at 0° C was added 4-bromo-ter-butylbenzene (10 g, 46.9 mmol) dropwise over 15 minutes. The reaction mixture was stirred at room temperature for one hour, poured into ice cold water and extracted with ethyl acetate. The organic fraction was washed with saturated sodium bicarbonate solution, saturated sodium chloride solution and dried over magnesium sulfate. The solvent was recovered under vacuum to obtain a yellow oil. The crude material was purified by chromatography on silica gel eluting with hexane/ethyl acetate (9:1) to afford the title compound (10.6 g, 87%) as a yellow oil.

B. 4-(1,1-Dimethylethyl)-2-nitrobenzonitrile

A solution of title A compound (10.6 g, 40.9 mmol) and copper(1)cyanide (6.47 g, 73.6 mmol) in N-methylpyrrolidinone (100 mL) was heated under argon at 175° C. for three hours. The reaction mixture was diluted with a large volume of diethyl ether and filtered. The filtrate was washed with 1N hydrochloric acid solution, saturated sodium bicarbonate, brine and dried over magnesium sulfate. The solvent was recovered under vacuum to obtain a brown oil. The crude material was chromatographed on silica eluting with hexane/ethyl acetate (4:1) to obtain the desired product (6.39 g, 77%) as a greenish solid.

C. 2-Amino-4-(1,1-Dimethylethyl)benzamide

A mixture of title B compound (3.0 g, 14.7 mmol) and stannous chloride dihydrate (16.6 g, 73.4 mmol) in ethanol (36 mL) was heated at reflux for one hour. The reaction mixture was poured onto ice/H2O and neutralized with solid sodium bicarbonate. The pH was adjusted to ca. 12 with sodium hydroxide solution and the mixture was extracted with ethyl acetate. The organic fraction was washed with brine, dried over magnesium sulfate and evaporated in vacuo to obtain the desired product (2.5 g, 90%) as a yellow solid.

D. 4-(1,1-dimethylethyl)-2-[[[(3-pyridinyl)amino]carbonyl] amino]-benzamide

A solution of title C compound (0.5 g, 2.60 mmol) and nicotinyl azide (0.47 g, 3.17 mmol) in toluene (10 mL) was heated at 85° C. for three hours. The solvent was recovered under vacuum to obtain a yellow solid. The crude product was purified by crystallization from isopropanol to obtain the title product (0.78 g, 87%) as an off-white solid, mp 188°–189° C. Analysis calculated for C17H20N4O2. 1.08C3H8O:C, 64.44; H, 7.65; N, 14.86. Found: C, 64.37; H, 7.62; N, 14.84

EXAMPLE 18

N-[2-Cyano-5-(1,1-dimethylethyl)phenyl]-N'-(3-pyridinyl)urea

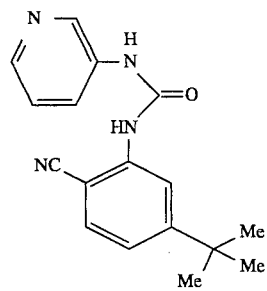

A. 2-Amino-4-(1,1-dimethylethyl)-benzonitrile

A solution of 4-(1,1-dimethylethyl)-2-nitrobenzonitrile (0.75 g, the title B compound of Example 17) in methanol (75 mL) containing 10% palladium on charcoal (0.75 g) was stirred under hydrogen gas at room temperature for 1.5 hours. The catalyst was filtered and the solvent was recovered under vacuum to obtain a dark colored gum. The crude material was chromatographed on silica eluting with hexane/methylene chloride (1:1) to obtain the desired product (0.47 g, 74%) as a colorless gum.

B. N-[2-Cyano-5-(1,1-dimethylethyl)phenyl]-N'-(3-pyridinyl)urea

A solution of nicotinyl azide(0.38 g, 2.55 mmol, prepared according to Saikachi, H and Kitagawa, T, *Chem. Pharm. Bull.*, 1977, 25 (7), 1651–1657) in toluene (7.5 mL) was heated at 85° C. for 15 minutes, after which time the title A compound (0.37 g, 2.12 mmol) was added. The reaction mixture was heated at 85° C. for 1.5 hours. The solvent was recovered under vacuum and the crude product was purified by chromatography on silica gel eluting with ethyl acetate/hexane (3:1) to afford the title compound (0.30 g, 48%) as an off-white solid, mp 164°–166° C. Analysis calculated for C17H18N4O.0.12 H2O: C, 68.86; H, 6.20; N, 18.90. Found: C, 68.76; H, 6.10; N, 19.00.

What is claimed is:

1. A compound of the formula

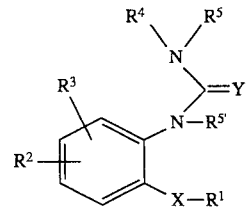

or pharmaceutically acceptable salts thereof wherein

X is a single bond, O, CO, S, NH or N(lower);

Y is O, S or NCN;

$R^1$ is cycloalkyl, aryl, or (aryl)alkyl;

$R^2$ is hydrogen, alkyl, haloalkyl, alkenyl, alkynyl, cycloalkyl, arylalkyl, (cycloalkyl)alkyl, —CN, —NO2, —COR, —COOR, —CONHR, —CONR6, —CF3, —S-alkyl, —SOalkyl, —SO2alkyl,

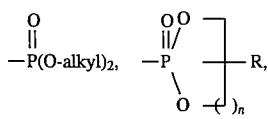

halogen, amino, substituted amino, —O-alkyl, —OCF$_3$, —OCH$_2$CF$_3$, —OCOalkyl, —OCONRalkyl, —NRCOalkyl, —NRCOOalkyl or —NRCONR$^6$, where R is hydrogen, alkyl, haloalkyl, aryl, arylalkyl, cycloalkyl or (cycloalkyl)alkyl;

R$^3$ is hydrogen, alkyl, hydroxy, —O-alkyl, amino, substituted amino, —NHCOR, —CN or —NO$_2$;

R$^4$ is heterocyclo;

R$^5$ and R$^{5'}$ are hydrogen, alkyl, or haloalkyl;

R$^6$ is hydrogen, hydroxy or —OCOR; and n is an integer of 1 to 3, provided that when R$^4$ is pyridyl, R$^1$ is alkyl, X is a single bond and Y is oxygen, then R$^2$ is —CN or —CONHR and that when R$^2$ is hydrogen then R$^3$ is other than hydrogen.

2. The compounds as recited in claim 1 wherein

X is a single bond, O or S;

Y is —O— or NCN;

R$^1$ is cycloalkyl or aryl;

R$^2$ is hydrogen, CN, NO$_2$, CONH$_2$, CF$_3$ or halo;

R$^3$ is hydrogen; and

R$^4$ is heterocyclo.

3. The compounds selected from the group consisting of

N-[5-cyano-2-(1,1-dimethylethyl)phenyl]-N'-(3-pyridinyl)urea;

N''-cyano-N-[5-cyano-2-(1,1-dimethylethyl)phenyl]-N'-(3-pyridinyl)guanidine;

N-[(4-chloro-3-pyridinyl)-N'-[5-cyano-2-(1,1-dimethylethyl)-phenyl]urea;

N-[5-cyano-2-(1,1-dimethylethyl)phenyl]-N'-(4-pyridinyl)urea;

N-[5-cyano-2-(1,1-dimethylethyl)phenyl]-N'-(2-pyridinyl)urea;

N-[4-cyano-(1,1'-biphenyl)-2-yl]-N'-(3-pyridinyl)urea;

N-(5-cyano-2-phenoxyphenyl)-N '-(3-pyridinyl)urea;

N-[2-(1-methylethoxy)-5-nitrophenyl]-N'-(3-pyridinyl)urea;

or pharmaceutically acceptable salts thereof.

4. A pharmaceutical composition comprising a compound of claim 1 and a pharmaceutically acceptable carrier.

5. A method for treating ischemia comprising administering to a mammalian specie in need thereof a therapeutically effective amount of a composition of claim 4.

* * * * *